(12) United States Patent
Hachfeld et al.

(10) Patent No.: US 6,486,949 B2
(45) Date of Patent: Nov. 26, 2002

(54) METHOD AND APPARATUS FOR EVALUATING THE QUALITY OF AN OPTICAL CRYSTAL

(75) Inventors: Klaus D. Hachfeld, Sturbridge, MA (US); Leonid D. Klebanov, Sturbridge, MA (US)

(73) Assignee: Corning Incorporated, Corning, NY (US)

( * ) Notice: Subject to any disclaimer, the term of this patent is extended or adjusted under 35 U.S.C. 154(b) by 113 days.

(21) Appl. No.: 09/803,281

(22) Filed: Mar. 9, 2001

(65) Prior Publication Data

US 2002/0105642 A1 Aug. 8, 2002

Related U.S. Application Data

(60) Provisional application No. 60/254,590, filed on Dec. 11, 2000.

(51) Int. Cl.[7] .................................................. G01N 21/64
(52) U.S. Cl. ........................................ 356/318; 250/458.1
(58) Field of Search .................................. 356/317, 318, 356/417; 250/458.1, 459.1, 461.1

(56) References Cited

U.S. PATENT DOCUMENTS

| | | | |
|---|---|---|---|
| 4,038,201 A | 7/1977 | Hargreaves | ................. 252/300 |
| 4,048,514 A | 9/1977 | Haussuehl et al. | ......... 307/88.3 |
| 4,053,572 A | 10/1977 | Moss et al. | ................. 423/490 |
| 4,101,331 A | 7/1978 | Anderson | ................... 106/73.1 |
| 4,461,572 A | * 7/1984 | Tsuchiya | ..................... 356/318 |
| 4,866,283 A | 9/1989 | Hill, Jr. | |
| 5,000,548 A | 3/1991 | Mercado | ..................... 354/414 |
| 5,459,313 A | 10/1995 | Schrader et al. | |
| 5,852,627 A | 12/1998 | Ershov | ........................ 372/108 |
| 5,856,991 A | 1/1999 | Ershov | ........................ 372/57 |
| 5,901,163 A | 5/1999 | Ershov | ........................ 372/102 |
| 5,970,082 A | 10/1999 | Ershov | ........................ 372/102 |
| 5,978,409 A | 11/1999 | Das et al. | ................... 372/100 |
| 5,982,800 A | 11/1999 | Ishihara et al. | ................ 372/57 |
| 6,069,749 A | 5/2000 | Omura | ........................ 359/727 |
| 2001/0043331 A1 | 11/2001 | Rebhan | ..................... 356/432 |

FOREIGN PATENT DOCUMENTS

| | | | |
|---|---|---|---|
| DE | 1 291 321 | 3/1969 | |
| DE | 222 426 A1 | 5/1998 | |
| EP | 0 875 778 A1 | 11/1998 | ........... G02B/13/14 |
| EP | 1 006 373 A2 | 6/2000 | |
| JP | 09-315894 | 12/1997 | |
| JP | 10[1998]-1310 | 1/1998 | ........... C01F/11/22 |
| JP | 10[1998]-59799 | 3/1998 | ........... C30B/29/12 |
| JP | 2001-033379 | 2/2001 | |
| JP | 2001-041876 | 2/2001 | |
| WO | 99/46836 | 9/1999 | ............. H01S/3/13 |

OTHER PUBLICATIONS

Warren J. Smith, Modern Optical Engineering, The Design of Optical Systems McGraw–Hill Book Company, 1966, pp. 145–355.

(List continued on next page.)

Primary Examiner—F. L. Evans
(74) Attorney, Agent, or Firm—Edward F. Murphy

(57) ABSTRACT

A method for evaluating the quality of an optical material includes obtaining a fluorescence spectrum of the optical material, obtaining a fluorescence spectrum of a reference material having desired performance in a target application, and determining whether a shape of the spectrum of the optical material is similar to a shape of the spectrum of the reference material. If the shape of the spectrum of the optical material is similar to the shape of the spectrum of the reference material, the method includes indicating that the optical material is suitable for the target application; otherwise, the method includes indicating that the optical material is unsuitable for the target application.

23 Claims, 6 Drawing Sheets

OTHER PUBLICATIONS

U.S. Ser. No. 09/327,043, filed Jun. 7, 1999, Gianoulakis et al., Crystal Growth and Annealing Method and Apparatus, pp. 1–21.
OPTOVAC, Optical Crystal Handbook, Jan. 1993, pp. 1–41.
Lambda Physik webpage; *http://www.lambdaphysik.com/ Microlithography* /fullstory.asp?news_id=22, Lithography News, Lambda Physik Ships Fifth 157nm Lithography Laser, page 1.
Lambda Physik webpage; *http://www.lambdaphysik.co*m/ Microlithography/novaline.asp, NovaLine® Lithography Series, pp. 1–2.
Lambda Physik webpage; *http://www.lambdaphysik.co*m/ Microlithography/mooreslaw.asp, Lithography—History, Moore's Law, pp. 1–3.
Lambda Physik webpage; *http://www.lambdaphysik.co*m/ Microlithography/fullstory.asp, Lithography News, Lambda Physik Announces Breakthrough in 157 nm F2 Lithography, pp. 1–2.
Chernevskya, E.G., et al., Optical Characteristics of Large Single Crystals of Fluorides, Opt. Technol. (USSR), Jun. 1973, vol. 40, No. 6, pp. 379–380.
Svelto, O., Principles of Lasers, $3^{rd}$ Ed., 1989, pp. 330–331.
Collier et al., Semiconductor fabrication drives deep–UV optics, Laser Focus World, Dec. 1998, pp. 63–70.
James Webb, All Calcium fluoride system uses 157–nm light, Laser Focus World, Sep. 2000, pp. 87–92.
Jiang: Growth Properties of Scintillating Crystala BaF2, Journal of Crystal Growth, vol. 79, No. 1–3, Dec. 1986, pp. 720–722.

* cited by examiner

METHOD AND APPARATUS FOR EVALUATING THE QUALITY OF AN OPTICAL CRYSTAL

CROSS-REFERENCE TO RELATED APPLICATIONS

This application claims priority from U.S. provisional application No. 60/254,590, filed Dec. 11, 2000.

BACKGROUND OF INVENTION

1. Field of the Invention

The invention relates generally to optical crystals for transmitting infrared, visible, and ultraviolet (UV) radiation. In particular, the invention relates to a method and an apparatus for evaluating the quality of an optical crystal.

2. Background Art

The trend in microelectronics is towards increasingly smaller scale. This is made possible by lithography techniques that can print fine patterns, allowing the development of integrated circuits that pack increasing density in the same area. The remarkable progress in lithography has been made possible by development in many fronts, including improved lens quality, increase in numerical aperture, improved resist processes, and the use of increasingly shorter exposure wavelengths. Currently, advanced microlithography systems use deep-UV radiation having a wavelength of 248 nm (KrF laser) to print 0.25-$\mu$m features. New microlithography systems using 193-nm radiation (ArF laser) and 157-nm radiation ($F_2$ laser) are actively under development and are expected to produce even smaller features. However, finding suitable lens materials for these shorter wavelengths poses a challenge. At present, high-purity fused silica and fluoride crystals are the practical choices for transmitting UV radiation. Development of 157-nm lithography requires fluoride crystals because the transmission properties of fused silica drops off significantly below 180 nm.

The performance required from fluoride crystal materials is not fully understood, yet the industry has to be served with components and materials that function properly. One of the several indicators that can be used to qualify a crystal material is fluorescence. Some laser manufacturers have found that the way a piece of fluoride crystal, especially calcium fluoride crystal, fluoresces may be linked to the way it performs in their excimer lasers. Some of these laser manufacturers have specified that crystal materials used in their lasers should be free of any visible fluorescence when exposed to deep-UV radiation (below 300 nm wavelength). It is not clear how laser performance is affected if the crystal material fluoresces. However, what is clear is that internal heating of the crystal material and durability of the material upon exposure to radiation at these wavelengths are important factors in lithography applications. For example, heating of the crystal material can change the refractive index of the material, resulting in phase shift errors imposed on the wavefront of a beam transmitted through the material. Optical lithography systems have very little tolerance for phase errors.

It should be noted that heating of the crystal material by passing a laser beam through it can have several mechanisms, only some of which may be accompanied by fluorescence. Thus, the aim is not to make a judgment about total losses by looking at fluorescence. Furthermore, it is not obvious that there is a connection between the fluorescence spectrum of the crystal and how constant the laser transmission remains as the laser beam continues to be passed into the crystal. Hence, finding the connection between fluorescence of the crystal and anything that really affects the performance of the crystal in the presence of the laser beam is still active research guided by measured correlated data. Notwithstanding the fact that the relationship between fluorescence of the crystal material and the laser performance is unclear, it would still be useful to have a mechanism for grading optical crystals based on fluorescence. Such grading may be one of the factors used in determining the suitability of the optical crystal for lithography applications or laser applications in general.

SUMMARY OF INVENTION

In one aspect, the invention relates to a method for evaluating the quality of an optical material. The method comprises obtaining a fluorescence spectrum of the optical material, obtaining a fluorescence spectrum of a reference material having desired performance in a target application, and determining whether a shape of the spectrum of the optical material is similar to a shape of the spectrum of the reference material. If the shape of the spectrum of the optical material is similar to the shape of the spectrum of the reference material, the method includes indicating that the optical material is suitable for the target application; otherwise, the method includes indicating that the optical material is unsuitable for the target application.

In another aspect, the invention relates to an apparatus for evaluating the quality of an optical material. The apparatus comprises a source which emits an excitation light and a plurality of optical elements which focus the excitation light on the optical material. The apparatus further includes a spectrometer which detects fluorescence light emitted from the optical material. A line of sight of the spectrometer is oriented at an angle with respect to a primary axis of the excitation light transmitted through the optical material. The apparatus further includes a processor which runs a process that compares the fluorescence data from the spectrometer to a reference fluorescence spectrum and determines the quality of the optical material based on the comparison.

Other aspects and advantages of the invention will be apparent from the following description and the appended claims.

DETAILED DESCRIPTION

Embodiments of the invention provide a method and an apparatus for evaluating the quality of an optical crystal. The method and apparatus of the invention allows an optical crystal to be classified under one of several optical grades once crystal growth is complete. The apparatus comprises a mechanism for obtaining a fluorescence spectrum of the optical crystal and comparing the fluorescence spectrum to the fluorescence spectrum of a reference crystal. Herein, the reference crystal has the same composition as the optical crystal to be evaluated and has the desired performance when exposed to electromagnetic radiation at a selected wavelength. The method allows a set of criteria to be defined and used to determine the closeness of the fluorescence spectrum of the optical crystal to the fluorescence spectrum of the reference crystal. If the fluorescence spectrum of the optical crystal is substantially similar to the fluorescence spectrum of the reference crystal, the optical crystal is considered to be a "good" crystal; otherwise, the optical crystal is considered to be a "bad" crystal. The assumption is that if the fluorescence spectrum of the optical crystal is substantially similar to the fluorescence spectrum of the reference crystal, the optical crystal will perform similarly to the reference crystal.

Figure 1:
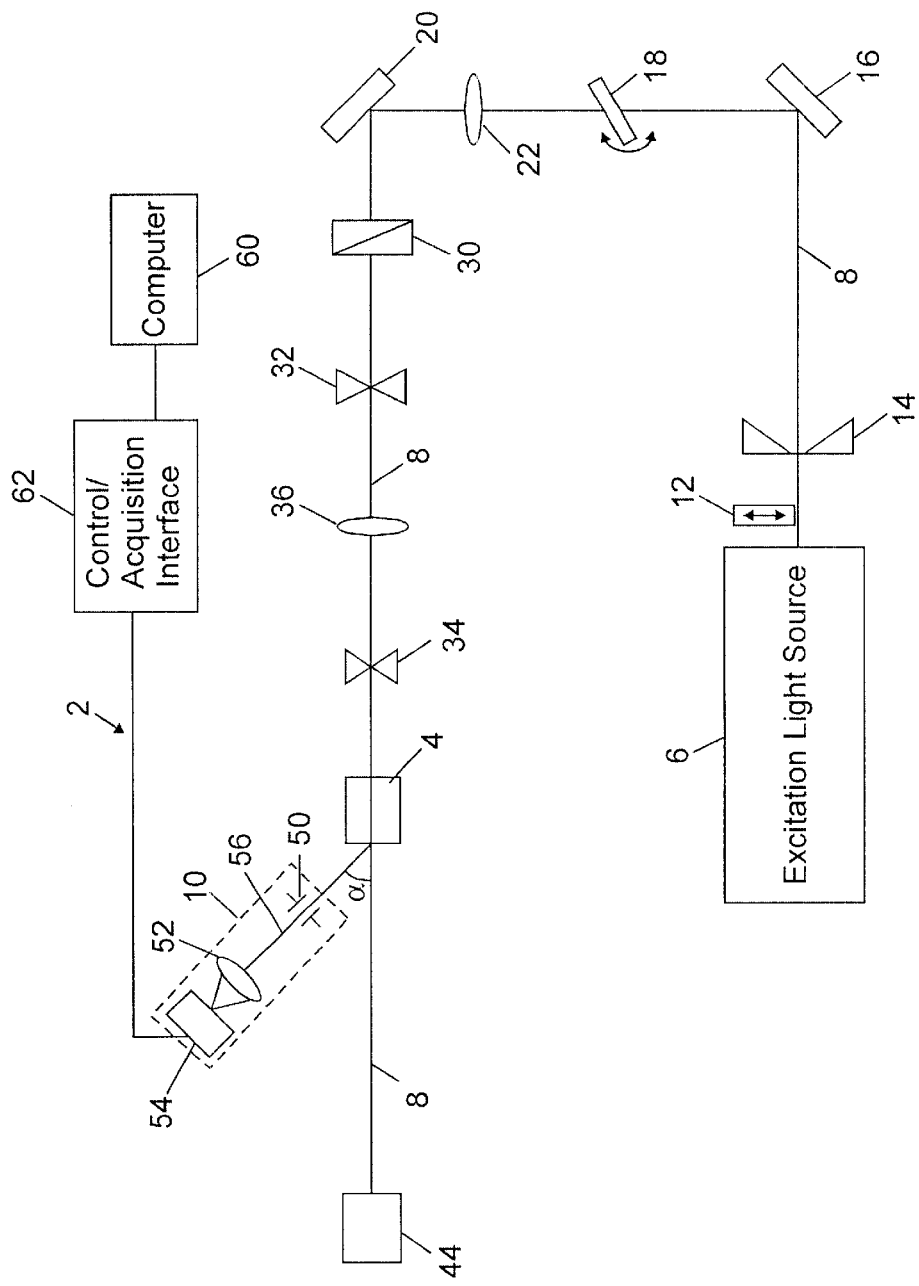
FIG. 1 is a schematic of an apparatus for measuring fluorescence of an optical material in accordance with one embodiment of the invention.

Various embodiments of the invention will now be described with reference to the accompanying drawings. FIG. 1 shows a schematic of an apparatus, generally referenced by numeral 2, for evaluating the quality of a test material 4 in accordance with one embodiment of the invention. The apparatus 2 includes an excitation light source 6 which produces the excitation light 8 that excites luminescent centers of the test material 4 and a fluorescence detector 10 which detects desired wavelengths (fluorescent light) emitted from the test material 4. In one embodiment, the test material 4 is a single fluoride crystal. Examples of single fluoride crystals include, but are not limited to, $CaF_2$, $SrF_2$, $BaF_2$, and $MgF_2$. In general, the test material 4 could be any crystal that is transparent at the desired operating wavelengths, e.g., below 300 nm. In another embodiment, the test material 4 is an optical element for transmitting electromagnetic radiation, e.g., a lithography lens. In another embodiment, the test material 4 is a laser component such as a beam expander, window, lens, output coupler, or prism, e.g., a line narrowing prism. In another embodiment, test material 4 is a blank (or preform) for fabricating a laser component or optical element. Such blanks are turned into components by processes such as shaping, grinding, cutting, cleaving, finishing, and polishing.

In the illustrated embodiment, the excitation light source 6 includes a randomly-polarized, ArF excimer laser which operates at 193-nm wavelength. The laser output beam comprises a train of laser pulses, each pulse having a predetermined length, e.g., a nominal 30 ns. However, the invention is not limited to use of a randomly-polarized, ArF excimer laser as the excitation light source 6. In general, the choice of excitation light source 6 and its operating wavelength will depend on the nature of the test material 4 and the intended area of application of the test material 4, i.e., the intended operating wavelengths of the test material. In alternate embodiments, light wavelengths such as 248 nm (KrF laser) or 157 nm ($F_2$ laser), or other suitable light wavelength may be used. Furthermore, it is not a requirement that the laser output beam comprises a train of pulses. A continuous wave laser could be used, for example. If the detection system 10 requires pulses, a beam chopper (not shown) may then be used to produce the pulses from the continuous wave laser output. Also, it is not a requirement that the laser is randomly polarized. More specific information may be obtained, for example, by linearly polarizing the laser beam and incorporating a polarization rotator, such as a half-wave plate, to orient the plane of polarization to suit the test.

A beam shutter 12 controls starting and stopping of the excitation light source 6.

When the excitation light source 6 is energized, excitation light or laser beam is projected through a variable rectangular aperture 14. The purpose of the variable rectangular aperture 14 is to clip the edges of the beam. The laser beam 8 is turned 90° by a beam bender 16. The laser beam 8 passes through a variable attenuator 18. The purpose of the variable attenuator 18 is to vary the intensity of the laser beam 8. The laser beam 8 is projected onto a beam bender 20 through an imaging lens 22. The beam bender 20 turns the laser beam 8 another 90°. The laser beam 8 then passes through a laser polarization scrambler 30 and a spatial mode filter 32. The polarization scrambler 30 ensures that the laser beam 8 is randomly polarizer, although this is not a requirement for practicing the principles of the invention. The spatial mode filter 32 smoothens out the laser beam 8 at the desired wavelengths. The filtered laser beam 8 is projected into a pinhole 34 by a lens 36 and then imaged on the test material 4.

The primary purpose of the elements 14, 18, 22, 30, 32, 34, and 36 is to condition the laser beam imaged on the test material 4. Depending on the quality of the laser beam produced by the source 6, one or more or all of these elements may be omitted. Furthermore, the source 6 can be aligned with the test material 4, eliminating the need for the beam benders 16, 20. In the illustrated embodiment, a nominal 1 mm diameter collimated beam propagates through the test material 4, although a smaller or larger diameter beam can be propagated through the test material. In one embodiment, the primary axis of the excitation laser beam 8 is aligned with the <11> crystallographic direction of the test material 4. The irradiating beam 8 transmitted through the test material 4 continues on its way to a laser dump 44.

The fluorescence detector 10 comprises one or more baffles 50, an imaging system 52, and a spectrometer (or spectrograph) 54. The baffle 50 restricts the field of view of the spectrometer 54 to the region of interest in the test material 4. The imaging system 52 projects the fluorescence light emitted from the test material 4 into the entrance pupil (not shown) of the spectrometer. The imaging system 52 may be an imaging lens, a zoom lens, or other type of lens.

The spectrometer 54 may be a general-purpose or fluorescence spectrometer. The S2000-series spectrometers from Ocean Optics, Inc., Dunedin, Fla., are examples of suitable spectrometers that can be used in the invention. However, the invention is not limited to these particular series of spectrometers. To improve the resolution of the data collected, the fluorescence detector 10 is aligned in such a way that no part of the irradiating beam 8 can enter the spectrometer 54. For example, the fluorescence detection axis 56 is oriented at an angle α with respect to the primary axis of the beam 8, where the angle α is greater than 0°. Preferably, the angle α is selected such that much of the internal volume of the test material 4 directly exposed to the laser beam can be viewed through the entrance pupil (not shown) of the spectrometer 54. Preferably the angle α. is selected such that the incident and exit surfaces of the test material are not visible through the entrance pupil (not shown) of the spectrometer. In general, the angle α can range from greater than 0° to 90°. As will be further explained below, the spatial resolution of the system improves as the angle α gets smaller. It should be noted that the fluorescence detector 10 can also be located on the incident side of the test material 4, as shown in FIG. 2, because the fluorescence generally radiates in all directions.

In operation, laser beam 8 from the excitation light source 6 is focused on the test material 4 through the pinhole 34. The beam 8 transmitted through the test material 4 goes into the laser dump 44. The fluorescence detector 10 detects the fluorescence light from the test material 4 and sends signals to a computer 60 through a control/acquisition interface 62. The computer 60 analyzes the data and displays the results. Such results may include the fluorescence spectrum of the test material 4 and data which indicates whether the test material 4 satisfies predefined criteria. In one embodiment, the computer 60 (or processor) runs a process which compares the fluorescence spectrum of the test material 4 to the fluorescence spectrum of a reference sample (not shown) in order to determine whether the test material 4 is suitable for a specific application. In one embodiment, a data acquisition application such as sold under the trade name LabVIEW, available from National Instruments, Austin, Tex., is loaded on the computer 60 and configured to receive the fluorescence data from the spectrometer 54 and to run the process which compares this fluorescence data to the fluorescence spectrum of the reference sample (not shown).

Because the fluorescence is excited each time the laser pulse passes through the test material (4 in FIGS. 1 and 2) and all fluorescing wavelengths are essentially excited simultaneously, the spectrometer (54 in FIGS. 1 and 2) should be designed in such a way that it is able to measure the total energy received in a defined wavelength increment ("channel") per laser pulse. Multi-channel spectrometers are commercially available, for example, from Ocean Optics, Inc. The signal in each channel is recorded and displayed as, for example, a complete spectrum by the computer 60. Further, signal-noise ratio enhancements may be achieved by integrating the signals in each channel over several laser pulses. Such enhancement of signal-to-noise by repetition is well known in the art. The enhancement of signal-to-noise ratio by repetitive acquisition is possible because real signals will add up with each data acquisition, while random noises will increase only with a square root of the number of repetitions ($\sqrt{n}$). Thus, the overall signal-to-noise ratio improves with the square root of the number of acquisition (i.e., S/N is proportional to $n/\sqrt{n}=\sqrt{n}$).

Figure 2:
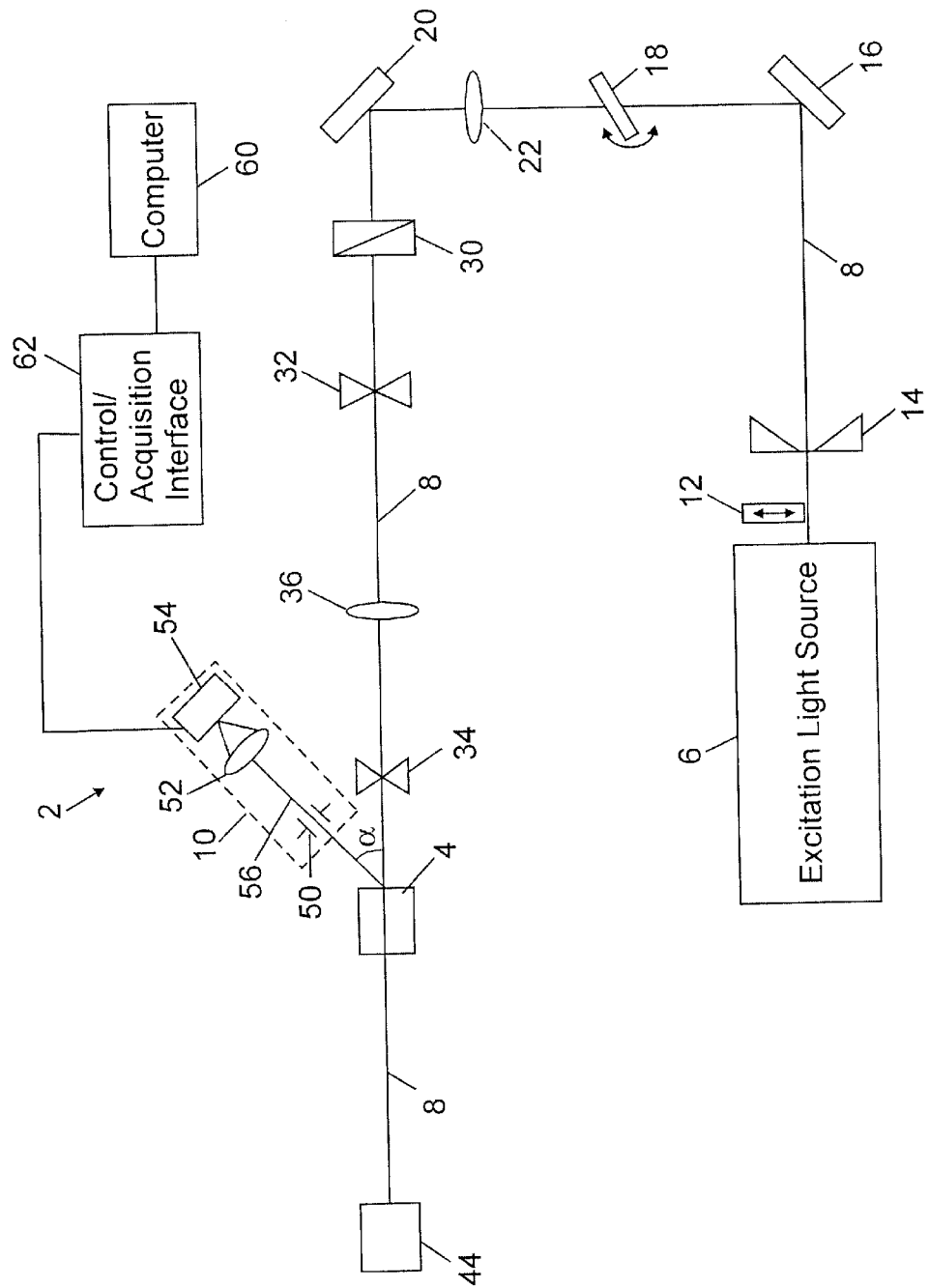
FIG. 2 shows the apparatus of FIG. 1 with the fluorescence detector located on the incident side of the test material.

Referring to FIGS. 1 and 2, further enhancements can be made by recognizing that fluorescence from the test material 4 will in general radiate in all directions, though not necessarily equally. The apparatus 2 will offer improved spatial resolution of the fluorescence spectrum if the fluorescence detection line of sight is close to the primary axis of the irradiating beam 8, i.e., the angle $\alpha$ is small. This gives large overlap of the volume region from which the spectrometer 54 receives primary fluorescence light which is directly excited by the laser beam 8. Correspondingly, secondary fluorescence, which is generated in the region outside the irradiating beam 8 by primary fluorescing photons at longer wavelengths than the laser beam, is limited. The essence is that the fluorescence spectrum displayed by the spectrometer 54 can be different if looking only at the secondary fluorescence, outside the irradiating beam 8, compared with the primary fluorescence spectrum generated within the region irradiated by the beam 8.

Further spectral enhancements can be achieved if the incident and exit surfaces of the test material 4 have a good optical polish so that the crystal structure shows minimal disturbance. It can be demonstrated with the system of the present invention that intense blue-green fluorescence is generated in calcium fluoride crystal if any part of the 193-nm beam 8 contacts a disturbed surface, such as the typically ground sides of the test material 4. As such, the angle $\alpha$ should be made small enough to ensure that light entering the spectrometer 54 can only come via polished test crystal surfaces. This further limits the secondary fluorescence from the surfaces of the test material 4.

Figure 3:
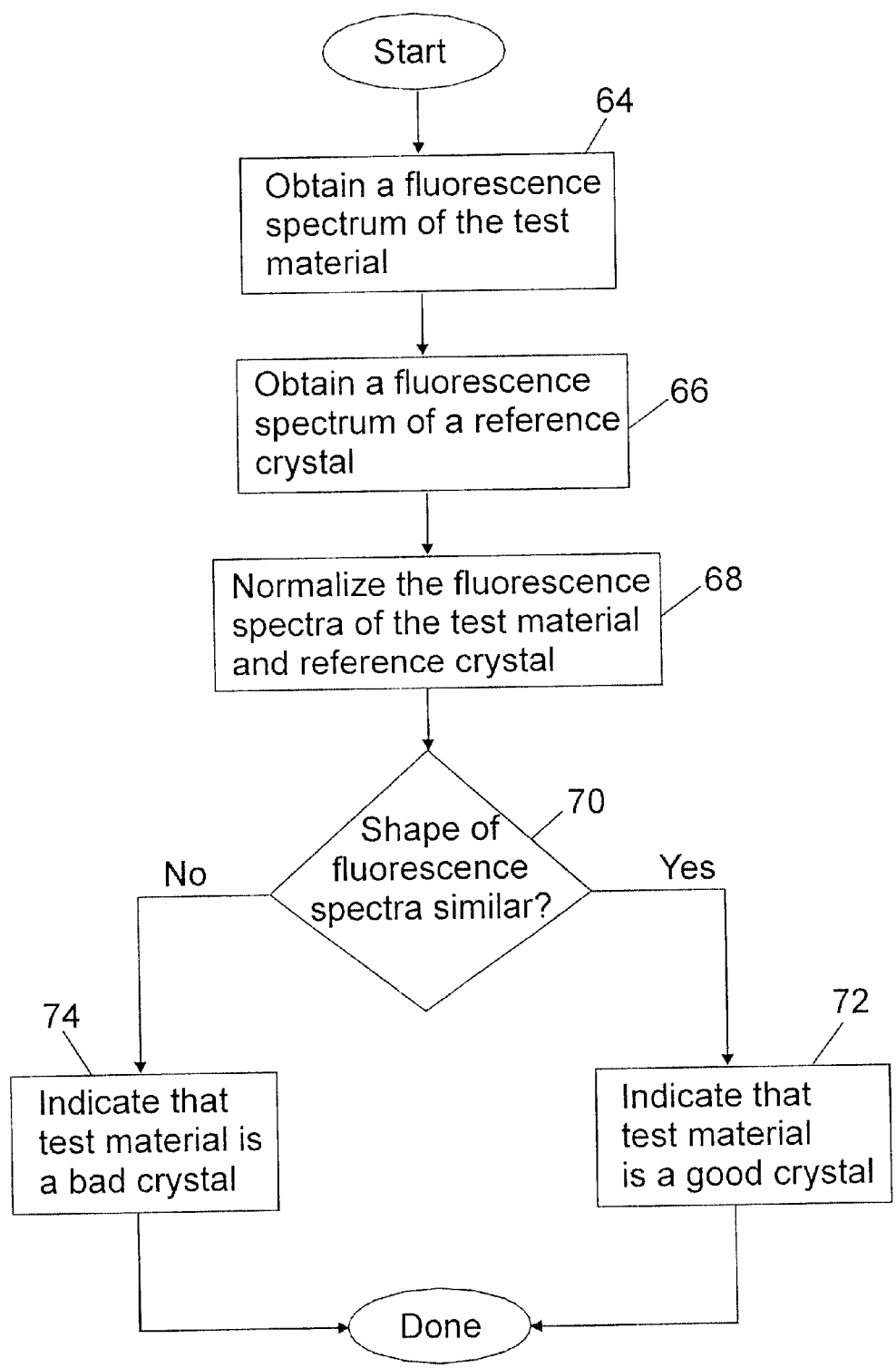
FIG. 3 is a flow chart of a process for evaluating the quality of an optical crystal in accordance with one embodiment of the invention.

FIG. 3 illustrates the process for evaluating the quality of a test material (4 in FIG. 1) according to one embodiment of the invention. The process starts, as indicated at 64, by obtaining a fluorescence spectrum of the test material (4 in FIG. 1), for example, using the apparatus shown in FIG. 1. Next, as indicated at 66, the fluorescence spectrum of a reference crystal is obtained. This reference crystal is considered as a good sample against which all others will be compared. "Good" in the sense of the reference crystal implies that material with this spectrum will characteristically be well-behaved in the target application, e.g., lithographic stepper and laser applications. For convenience, the fluorescence spectrum of the test material (4 in FIG. 1) will be referred to as the test spectrum and the fluorescence spectrum of the reference crystal will be referred as the reference spectrum.

As indicated at 68, the reference spectrum and the test spectrum are normalized. Normalization can be achieved by scaling one spectrum or both spectra so that a "reference peak" will have the same intensity on the spectra at a selected wavelength. The "reference peak" is usually one selected from those that are independent of the property that is being compared between the reference crystal and the test material. The shapes of the normalized spectra are compared, as indicated at 70, in order to determine whether they are similar. The degree of similarity between the two spectra is determined by a set of predefined criteria. If the shapes of the spectra are similar (indicated at 72), then the test material (4 in FIG. 1) should behave similarly to the reference sample. In this case, the test material (4 in FIG. 1) is considered to be a "good" crystal and is suitable for use in the target application. If the shapes of the spectra are dissimilar (indicated at 74), the test material is considered to be a "bad" crystal.

In the examples which follow, four criteria are defined for the purpose of determining similarity between the reference spectrum and the test spectrum. The reference sample is a $CaF_2$ crystal that is known to have desirable performance for a target application, e.g., lithographic stepper and laser applications. Table 1 summarizes the test criteria. The test material is considered to be suitable for the target application if all criteria are satisfied. If any of the criteria fails, the test material is considered to be unsuitable for the selected application. The process can be expanded to include specification of a degree of success or failure. This can be used to classify the test material into one of several optical grades. It should be noted that more or less or different test criteria can be defined without invalidating the concept of the method.

TABLE 1

Criteria for Evaluating Optical Crystal

| Criterion | Description |
|---|---|
| A | The test and reference spectra have self-trapped exciton peaks centered at certain wavelengths. In the normalized test and reference spectra shown in FIGS. 4–6, for example, the self-trapped exciton peaks are centered at approximately 330 nm. This criterion specifies that the line shapes of the self-trapped exciton peaks for the test and reference spectra should not differ by more than a predefined factor, e.g., 500 in arbitrary units. |
| B | This criterion specifies that the total area under the fluorescence curve in the blue-green part of the test spectrum should not exceed a predefined amount, e.g., 493 in arbitrary units. |
| C | This criterion specifies that the total area under the fluorescence curve in the red part of the test spectrum should not exceed a predefined amount, e.g., 100 in arbitrary units. |
| D | This criterion specifies that the total area under the fluorescence curve in the infrared part of the test spectrum should not exceed a predefined amount, e.g., 171 in arbitrary units |

The following examples are intended for illustration purposes and are not intended to limit the scope of the invention as otherwise described herein.

EXAMPLE 1

Figure 4:
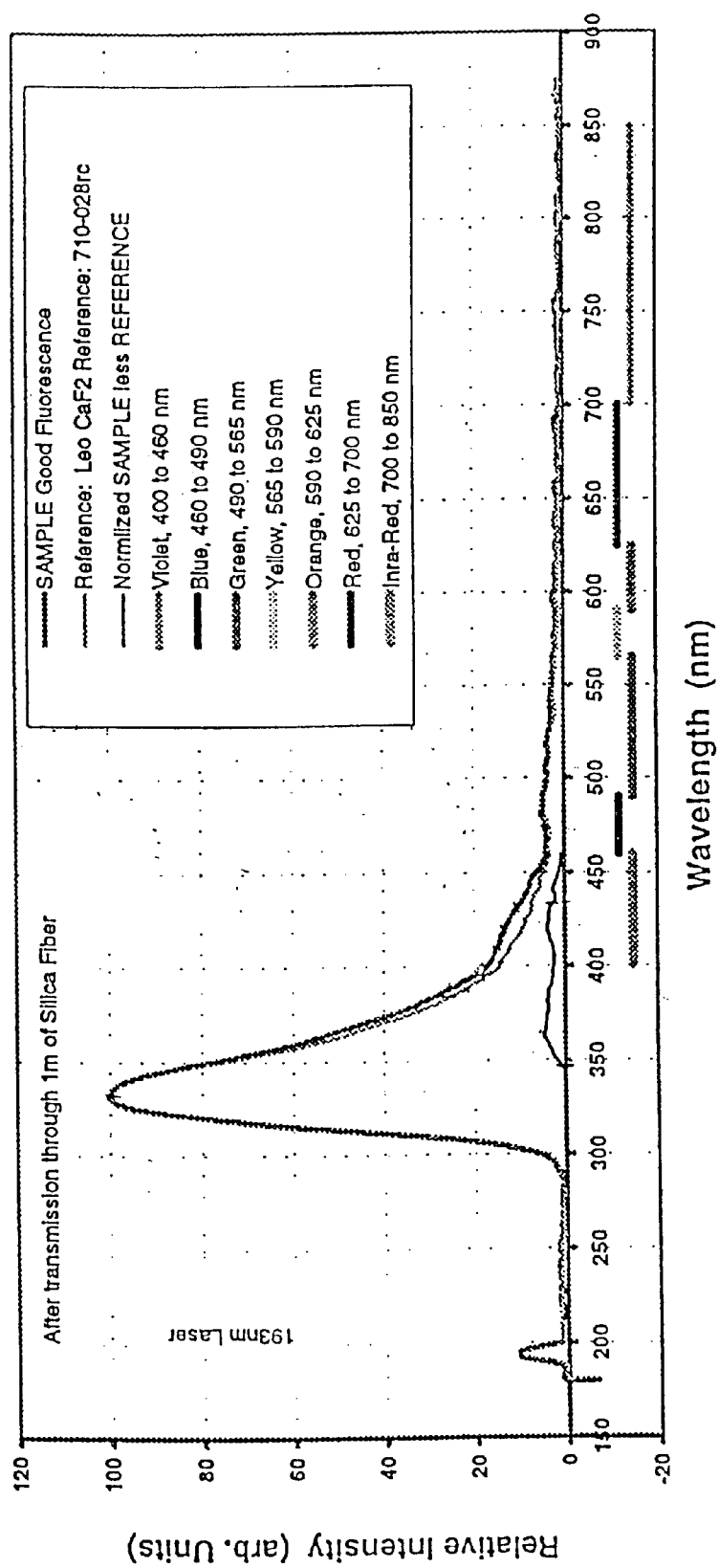
FIG. 4 shows fluorescence spectra of a good $CaF_2$ crystal and a reference $CaF_2$ crystal.

FIG. 4 shows a test spectrum T superimposed on a reference spectrum R. The test spectrum T is for $CaF_2$ crystal irradiated with 193-nm laser light. The reference spectrum R is for a reference $CaF_2$ crystal which has desirable performance in excimer laser applications. The test and reference spectra T, R have been normalized using a reference peak of approximately 330 nm. The area under the test spectrum T ("test area") in the 335 nm to 850 nm wavelength range is 4,787 in normalized arbitrary units. The area under the reference spectrum R ("reference area") in the 335 nm to 850 nm wavelength range is 4,369 in normalized arbitrary units.

To determine whether criterion A is satisfied, only the line shapes of the trailing edges of the self-trapped exciton peaks, i.e., from 335 nm to 460 nm, are compared. For more detailed analysis, the line shapes of both the leading edges and trailing edges of the peaks may be compared. The line shapes are compared by calculating the area between the test and reference spectra T, R ("difference area") in the wavelength range 335 nm to 460 nm. The difference area was determined to be 330 in normalized arbitrary units, which is below the predefined limit of 500 specified in Table 1. Therefore, criterion A is satisfied. For the purposes of grading the test crystal, the ratio of the difference area to the predefined limit may indicate the degree of similarity between the reference spectrum R and the test spectrum T.

Criterion B relates to the fluorescence intensity in the blue-green region (around 460 nm–565 nm). This fluorescence intensity is determined by calculating the area under the fluorescence curve in the blue-green region. The cut-off value for the fluorescence intensity in this region is set at 493 in arbitrary units. Typically, the cut-off value is derived from a value predetermined with a batch of good crystals plus a desired margin. For the reference spectrum R, the area in the blue-green region is 352 arbitrary units, which is below the cut-off value of 493. For the test spectrum T, the area in the blue-green region is 374 in arbitrary units, which is below the cut-off value of 493. Thus, criterion B is satisfied.

Similarly, the test sample passes criterion C (red fluorescence in the region of 625–700 nm) and criterion D (infrared fluorescence in the region of 700–850 nm). Based on the results, the test material having the spectrum T shown in FIG. 4 is a good crystal and is suitable for the target application, i.e., for use in excimer laser. The ratio of fluorescence intensity to predefined limit for the various wavelength ranges can indicate degree of similarity between the test crystal and the reference sample. This ratio can be used to grade the test crystal. Table 2 summarizes the results.

TABLE 2

Fluorescence Spectrum Data for Example 1

| Criteria | Reference (area, arbitrary units) | Test Sample (area, arbitrary units) | Area Limit (arbitrary units) | Pass or Fail |
|---|---|---|---|---|
| B | 352 | 374 | 493 | Pass |
| C | 77 | 97 | 100 | Pass |
| D | 114 | 139 | 171 | Pass |
| A | Difference (Area, Limit) = (330, 500) | | | Pass |

EXAMPLE 2

Figure 5:
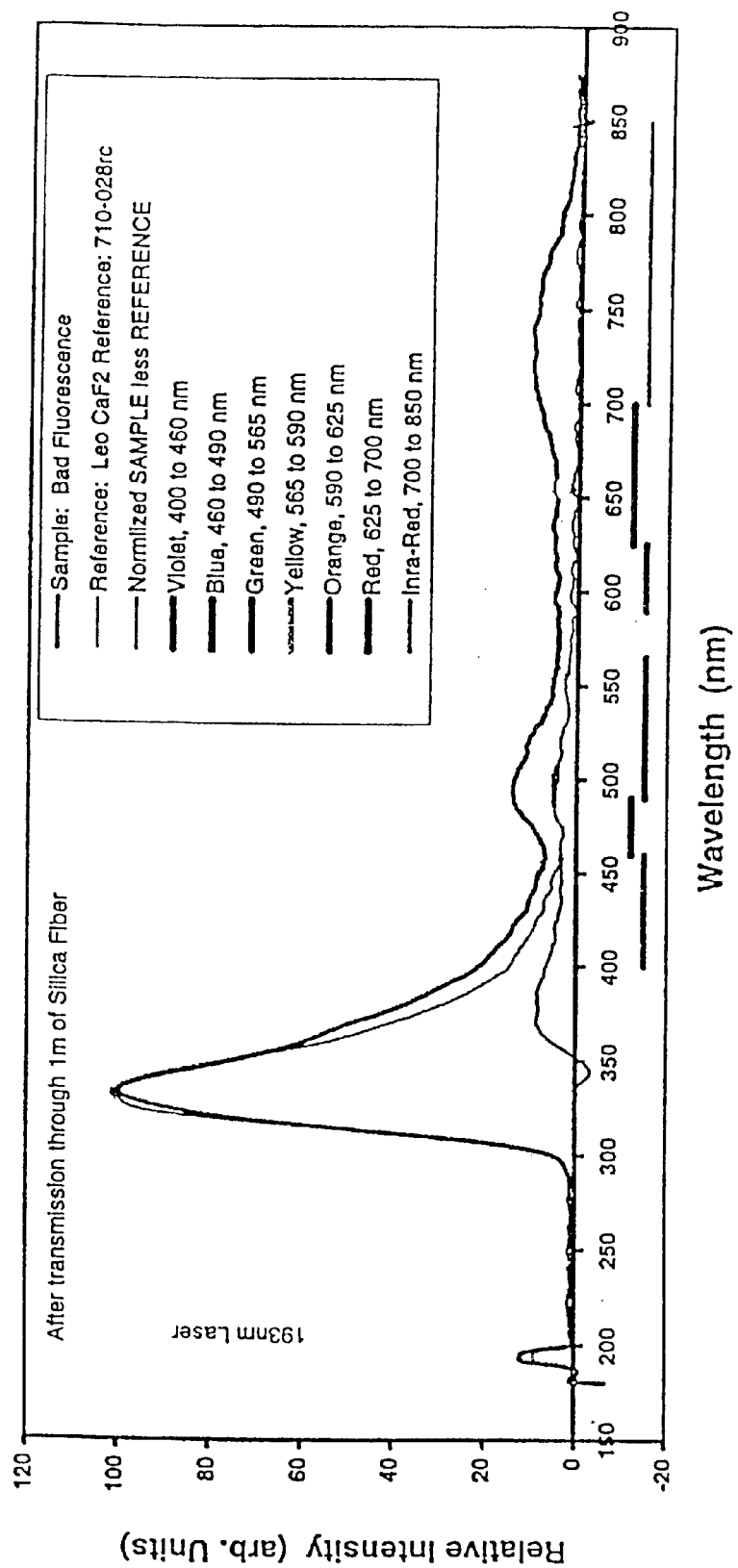
FIG. 5 shows fluorescence spectra of a bad $CaF_2$ crystal and a reference $CaF_2$ crystal.

FIG. 5 shows a test spectrum T superimposed on a reference spectrum R. The test spectrum T is for $CaF_2$ crystal irradiated with 193-nm laser light. The reference spectrum R is for a reference $CaF_2$ crystal which has desirable performance in excimer laser applications. The test and reference spectra T, R have been normalized using a reference peak of approximately 330 nm. The area under the test spectrum T ("test area") in the 335 nm to 850 nm wavelength range is 6,981 in normalized arbitrary units. The area under the reference spectrum R ("reference area") in the 335 nm to 850 nm wavelength range is 4,369 in normalized arbitrary units.

To determine whether criterion A is satisfied, the area between the test and reference spectra T, R ("difference area") in the 335 nm to 460 nm wavelength range is calculated. The difference area was determined to be 554 in normalized arbitrary units, which is higher than the predefined limit of 500 stated in Table 1. Because the difference area is greater than the predefined limit, criterion A is not satisfied. Failure of this criterion alone is sufficient to declare the test material in this example as unsuitable for the intended application.

Criterion B relates to the fluorescence intensity in the blue-green region (around 460 nm–565 nm). For the reference spectrum R, the fluorescence intensity in the blue-green region is 352 arbitrary units. For the test spectrum T, the fluorescence intensity in the blue-green region is 980 arbitrary units, which is much greater than the cut-off value of 493 in arbitrary units. Again, criterion B is not satisfied. Similarly, this test sample fails criterion C (red fluorescence in the region of 625–700 nm) and criterion D (infrared fluorescence in the region of 700–850 nm). Based on the results, the test material having the test spectrum T shown in FIG. 5 is a bad crystal and is unsuitable for the intended application, i.e., for use in excimer laser. Table 3 summarizes the results.

TABLE 3

Fluorescence Spectrum Data for Example 2

| Criteria | Reference (area, arbitrary units) | Test Sample (area, arbitrary units) | Area Limit (arbitrary units) | Pass or Fail |
| --- | --- | --- | --- | --- |
| B | 352 | 980 | 493 | Fail |
| C | 77 | 455 | 100 | Fail |
| D | 114 | 968 | 171 | Fail |
| A | Difference (Area, Limit) = (554, 500) | | | Fail |

EXAMPLE 3

Figure 6:
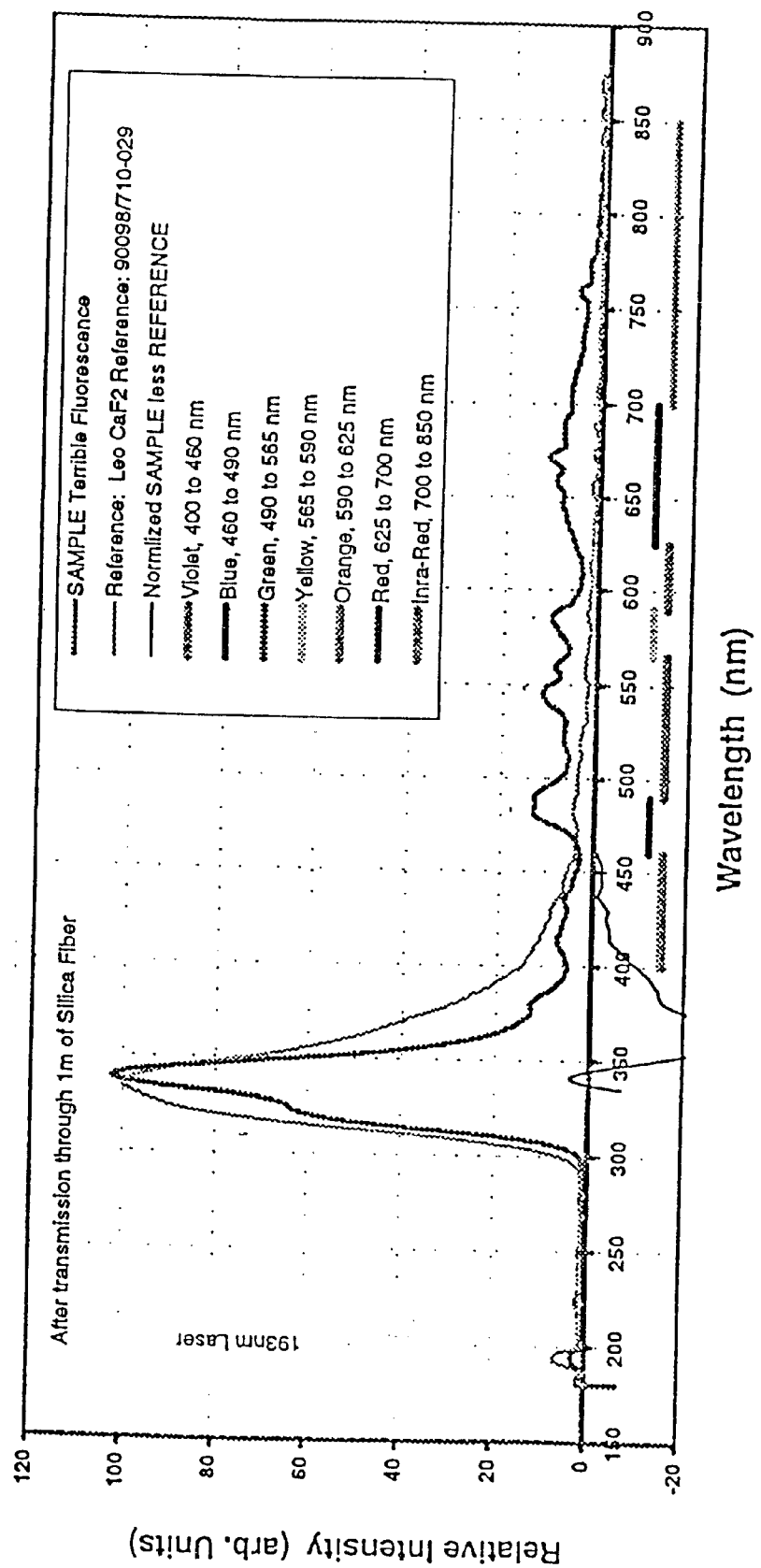
FIG. 6 shows fluorescence spectra of a bad $CaF_2$ crystal and a reference $CaF_2$ crystal.

FIG. 6 shows a test spectrum T superimposed on a reference spectrum R. The test spectrum T is for CaF$_2$ crystal irradiated with 193-nm laser light. The reference spectrum R is for a reference CaF$_2$ crystal which has desirable performance in excimer laser applications. The test and reference spectra T, R have been normalized using a reference peak of approximately 330 nm. The area under the test spectrum T ("test area") in the 335 nm to 850 nm wavelength range is 4,722 in normalized arbitrary units. The area under the reference spectrum R ("reference area") in the 335 nm to 850 nm wavelength range is 4,337 in normalized arbitrary units.

To determine whether criterion A is satisfied, the area between the test and reference spectra T, R ("difference area") in the 335 nm to 460 nm wavelength range is calculated. The difference area was determined to be –1,194 in normalized arbitrary units, the absolute value of which is higher than the predefined limit of 500 stated in Table 1. The negative value indicates that the test spectrum T is below the reference spectrum R in this region. Based on the difference in area over the 335 nm to 460 nm wavelength range, this test sample fails criterion A.

Criterion B relates to the fluorescence intensity in the blue-green region (around 460 nm–565 nm). The area under the reference spectrum R in this region is 319 arbitrary units. The area under the test spectrum T in this region is 839 arbitrary units, which is greater than the cut-off value of 493 arbitrary units. Thus, criterion B is not satisfied. Similarly, this test sample fails criterion C (red fluorescence in the region of 625–700 nm) and criterion D (infrared fluorescence in the region of 700–850 nm). Based on the results, the test material having the test spectrum T shown in FIG. 6 is a bad crystal and is unsuitable for the intended application, i.e., for use in excimer laser. Table 4 summarizes the results.

TABLE 4

Fluorescence Spectrum Data for Example 3

| Criteria | Reference (area, arbitrary units) | Sample (area, arbitrary units) | Area Limit (arbitrary units) | Pass or Fail |
| --- | --- | --- | --- | --- |
| B | 319 | 839 | 493 | Fail |
| C | 79 | 577 | 100 | Fail |
| D | 117 | 437 | 171 | Fail |
| A | Difference (Area, Limit) = (–1,149, 500) | | | Fail |

It should be noted that for the test samples shown in FIGS. 4 and 5, the line shapes of the leading edges of the self-trapped exciton peaks of the test and reference spectra T, R are practically the same. For the test sample shown in FIG. 5, there is a significant difference between the line shapes of the leading edges of the self-trapped exciton peaks of the test and reference spectra T, R. This seems to indicate that it may be worthwhile to include a comparison of the line shapes of the leading edges of the self-trapped exciton peaks in the analysis. As previously mentioned, the criteria can be adjusted as necessary to determine which crystals are good or bad from a fluorescence analysis perspective.

In another embodiment of the invention, the fluorescence lifetime can be used as a criterion for quality control. After a pulsed excimer irradiation, the intensity of fluorescence will typically decay exponentially. If a particular peak arises from a composite of several different fluorescent species, the overall decay of this composite peak will likely deviate from an exponential curve and the apparent lifetime will change. Therefore, fluorescence lifetime can be a useful criterion. For lifetime determination, it is preferable to monitor strong fluorescence peak using a pulsed incident beam. However, as described earlier, a continuous wave laser and a beam chopper can be used to provide a similar "pulsed" irradiation. In the example using CaF$_2$ crystals, the signals around 350–400 nm may be good candidates for lifetime measurement. This is because the spectral shape changes in the 350–400 nm region, suggesting that the fluorescent species responsible for the fluorescence in this region are very different between the samples used in FIGS. 3–5. These different fluorescent species are expected to have different decay curves and, therefore, different lifetimes.

The invention provides general advantages. The apparatus 2 described in FIG. 1 can measure the fluorescence of a test material. Using the process described in FIG. 3, the fluorescence data of the test material can be analyzed to determine whether the test material will behave similarly to a reference crystal in a target application. The reference crystal is selected to be a material that has desirable performance for the intended application and has the same composition as the test material. If the fluorescence spectra of the test material and reference crystal are similar, the test material is expected to behave in a similar manner to the reference crystal for the intended application. The degree of similarity between the reference material and the test material can be used to classify the test material into one of several optical grades.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for evaluating the quality of an optical material, comprising:
    obtaining a fluorescence spectrum of the optical material;
    obtaining a fluorescence spectrum of a reference material having desired performance in a target application;
    determining whether a shape of the spectrum of the optical material is similar to a shape of the spectrum of the reference material; and
    if the shape of the spectrum of the optical material is similar to the shape of the spectrum of the reference material, indicating that the optical material is suitable for the target application;
    otherwise, indicating that the optical material is unsuitable for the target application.

2. The method of claim 1, wherein determining whether a shape of the spectrum of the optical material is similar to a shape of the fluorescence spectrum of the reference material comprises normalizing the fluorescence spectra of the optical material and reference material at a selected wavelength.

3. The method of claim 2, further including determining a difference in the areas under the fluorescence spectra of the optical material and the reference material.

4. The method of claim 3, wherein the shape of the fluorescence spectrum of the optical material is similar to the shape of the fluorescence spectrum of the reference material if the difference in areas does not exceed a specified limit.

5. The method of claim 2, further including determining a difference in the areas under a selected region of the fluorescence spectra of the optical material and the reference material.

6. The method of claim 5, wherein the shape of the fluorescence spectrum of the optical material is similar to the shape of the fluorescence spectrum of the reference material if the difference in areas does not exceed a specified limit.

7. The method of claim 6, wherein the selected region corresponds to the blue-green part of the fluorescence spectra.

8. The method of claim 6, wherein the selected region corresponds to the red part of the fluorescence spectra.

9. The method of claim 6, wherein the selected region corresponds to the infrared part of the fluorescence spectra.

10. The method of claim 1, wherein obtaining a fluorescence spectrum of the optical material comprises exciting luminescent centers of the optical material and measuring an intensity of the fluorescent light emitted from the optical material.

11. The method of claim 10, wherein exciting luminescent centers comprises focusing a laser beam on the optical material.

12. The method of claim 11, wherein a line of detection of the fluorescent light is oriented at an angle with respect to a primary axis of the laser beam.

13. The method of claim 12, wherein the angle is greater than 0 degree but less than 90 degrees.

14. The method of claim 11, wherein the optical material and reference material are single crystals.

15. The method of claim 14, wherein a primary axis of the laser beam is aligned with a <111> crystallographic direction of the optical material.

16. The method of claim 1, wherein the optical material and reference material are fluoride crystals.

17. The method of claim 1, wherein the optical material and reference material are $CaF_2$ crystals.

18. The method of claim 1, wherein the optical material is a preform for an optical element which transmits electromagnetic radiation.

19. The method of claim 1, wherein the optical material is a preform for a laser component.

20. The method of claim 19, wherein the laser component is selected from the group consisting of prism, beam expander, window, lens, and output coupler.

21. An apparatus for evaluating the quality of an optical crystal, comprising:
    a source which emits an excitation light;
    an optical element which focuses the excitation light on the optical crystal;
    a spectrometer which detects fluorescence light emitted from the optical crystal, the spectrometer having a line of sight oriented at an angle with respect to a primary axis of the excitation light transmitted through the optical crystal; and
    a processor running a process which compares the fluorescence data from the spectrometer to a reference fluorescence spectrum and determines the quality of the optical crystal based on the comparison.

22. The apparatus of claim 21, wherein the source is an excimer laser.

23. The apparatus of claim 21, wherein the angle is greater than 0 degree but less than 90 degrees.

* * * * *